(12) United States Patent
Ginsberg

(10) Patent No.: US 7,570,980 B2
(45) Date of Patent: Aug. 4, 2009

(54) APPARATUS AND METHOD FOR MONITORING BLOOD GLUCOSE LEVELS INCLUDING CONVENIENT DISPLAY OF BLOOD GLUCOSE VALUE AVERAGE AND CONSTITUENT VALUES

(75) Inventor: Barry H. Ginsberg, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 982 days.

(21) Appl. No.: 10/658,209

(22) Filed: Sep. 10, 2003

(65) Prior Publication Data

US 2004/0059201 A1 Mar. 25, 2004

Related U.S. Application Data

(60) Provisional application No. 60/409,965, filed on Sep. 11, 2002.

(51) Int. Cl.
*A61B 5/00* (2006.01)
(52) U.S. Cl. ..................... 600/347; 600/365
(58) Field of Classification Search ........... 600/204, 600/365, 600, 300, 301, 364, 316, 347
See application file for complete search history.

(56) References Cited

U.S. PATENT DOCUMENTS

| | | | | |
|---|---|---|---|---|
| 4,475,158 A | | 10/1984 | Elias | |
| 4,731,726 A | * | 3/1988 | Allen, III | 600/300 |
| 4,838,275 A | | 6/1989 | Lee | 128/670 |
| 5,108,889 A | * | 4/1992 | Smith et al. | 435/4 |
| 5,251,126 A | * | 10/1993 | Kahn et al. | 600/309 |
| 5,307,263 A | | 4/1994 | Brown | 364/413.09 |
| 5,410,474 A | | 4/1995 | Fox | 364/413.07 |
| 5,536,249 A | | 7/1996 | Castellano et al. | 604/65 |
| 5,593,390 A | | 1/1997 | Castellano et al. | 604/187 |
| 5,665,215 A | | 9/1997 | Bussmann et al. | 204/403 |
| 5,822,715 A | | 10/1998 | Worthington et al. | 702/19 |
| 5,899,855 A | | 5/1999 | Brown | 600/301 |

(Continued)

FOREIGN PATENT DOCUMENTS

DE 43 15 532 A1 11/1993

(Continued)

*Primary Examiner*—Robert L Nasser
(74) *Attorney, Agent, or Firm*—Roylance, Abrams, Berdo & Goodman, L.L.P.

(57) ABSTRACT

A method of presenting glucose data to a person with diabetes from a blood glucose meter is provided in which an effective meal average (EMA) value is presented, followed by two or more of the individual values that make up the EMA, to provide improved feedback data for clinical decisions by patients who need to alter their dose of insulin. The EMA can also comprise a measure of the variability of its constituent values. The EMA encompasses those values that occur at specified times such as 1 hour before and 1 hour after a specified meal time. The EMA is calculated over a limited number of days previous to the calculation (e.g., 3 days) and has a minimum number of values that must be obtained within the time and date ranges. An algorithm allows for exclusion of any given reading from the average (e.g., post-prandial or control solution readings). Patients can use 1 to 8 EMA on any given date range (e.g., preferably 4, that is, breakfast, lunch, supper and bedtime snack).

28 Claims, 7 Drawing Sheets

U.S. PATENT DOCUMENTS

| | | | |
|---|---|---|---|
| 6,024,699 A | 2/2000 | Surwit et al. | 600/300 |
| 6,027,459 A | 2/2000 | Shain et al. | 600/573 |
| 6,113,537 A | 9/2000 | Castano | 600/300 |
| 6,124,134 A | 9/2000 | Stark | |
| 6,159,155 A | 12/2000 | Nevo et al. | 600/483 |
| 6,277,071 B1 | 8/2001 | Hennessy et al. | 600/300 |
| 6,368,272 B1 | 4/2002 | Porumbescu | 600/300 |
| 6,379,301 B1 | 4/2002 | Worthington et al. | 600/309 |
| 6,424,847 B1 | 7/2002 | Mastrototaro et al. | 600/316 |
| 6,425,863 B1 | 7/2002 | Werner et al. | 600/365 |
| 6,558,320 B1 * | 5/2003 | Causey et al. | 600/300 |
| 6,579,690 B1 | 6/2003 | Bonnecaze et al. | 435/14 |
| 6,589,229 B1 | 7/2003 | Connelly et al. | 604/890.1 |
| 6,604,050 B2 | 8/2003 | Trippel et al. | 702/19 |
| 6,607,658 B1 | 8/2003 | Heller et al. | 205/777.5 |
| 2002/0022773 A1 * | 2/2002 | Drinan et al. | 600/300 |
| 2003/0125612 A1 * | 7/2003 | Fox et al. | 600/347 |
| 2003/0216628 A1 * | 11/2003 | Bortz et al. | 600/365 |
| 2005/0059895 A1 * | 3/2005 | Brown | 600/481 |

FOREIGN PATENT DOCUMENTS

| | | |
|---|---|---|
| EP | 1 369 688 A | 12/2003 |

* cited by examiner

APPARATUS AND METHOD FOR MONITORING BLOOD GLUCOSE LEVELS INCLUDING CONVENIENT DISPLAY OF BLOOD GLUCOSE VALUE AVERAGE AND CONSTITUENT VALUES

This application claims priority from U.S. Provisional Application Ser. No. 60/409,965 filed Sep. 11, 2002, the contents of which are expressly incorporated herein by reference in their entirety.

CROSS-REFERENCE TO RELATED APPLICATIONS

Related subject matter is disclosed in a copending U.S. patent application of Gordon et al, entitled "A System and Method for Integrating Data with Guidelines to Generate Displays Containing the Guidelines and Data", Ser. No. 09/985,173, filed Nov. 1, 2001; and in a copending U.S. patent application of Gordon, entitled "System and Method for Assessment and Corrective Action Based on Guidelines", Ser. No. 10/153,883, filed May 24, 2002; the entire contents of both applications being incorporated herein by reference.

FIELD OF THE INVENTION

The invention relates generally to blood glucose meters and glucose monitoring for managing diabetes and, more particularly, to presentation of glucose data to a user in a convenient format, including an effective meal average and its constituent values and/or a measure of variability among the constituent values.

BACKGROUND OF THE INVENTION

A number of blood glucose monitoring systems are available which generally include a blood glucose meter. The blood glucose meter can be configured to receive and read a test strip inserted therein on which a drop of a patient's blood has been deposited, or can be adapted for subcutaneous readings, for example.

Blood glucose meters generally comprise a memory for storing measured blood glucose values, along with other data such as the corresponding dates and times of day the values were measured. Blood glucose meters are generally also provided with a display screen, and user input buttons with which a user can specify which of the stored values to display.

Some blood glucose meters also provide statistical data relating to the stored measured blood glucose values such as 7-day, 14-day and 30-day averaging of glucose levels at one or more selected times of day (e.g., breakfast, lunch, dinner and nighttime). Examples of such blood glucose meters are Accu-check meters available from Roche Diagnostics USA and One Touch meters available from LifeScan. These blood glucose meters, however, are disadvantageous because the length of the period of time over which the averages are calculated is too long when a patient is using the averaging to adjust his insulin dosage, and particularly when the current average blood glucose values are too low.

The Ascensia Dex2 glucose meter available from Bayer Healthcare provides four daily averages, that is, averages of measured blood glucose values taken during a particular period of time such as a two hour window around a selected mealtime. No existing blood glucose meter, however, provides an average blood glucose value over a selected bin or period of time, as well as convenient access to the constituent values used to derive the average value and optionally an indication of variability among the constituent values. As will be described in more detail below, an indication of variability or at least knowledge of constituent values used to derive a mealtime average, is important information to have when adjusting insulin dosage.

Blood glucose monitoring can be combined with a diabetes management system comprising software (e.g., for installation on a personal computer (PC) or personal data assistant (PDA)) for collecting and analyzing meter readings and generating summaries and graphical results (e.g., pie charts, histograms and the like) to assist the patient in understanding trends in their blood glucose levels and insulin regimen. These systems, however, also do not provide a patient with immediate and convenient access to averages of blood glucose levels at a mealtime or during another specified time period and to the constituent levels used to generate these averages. For example, the One Touch diabetes management software available from LifeScan can provide mealtime averages in a computer generated logbook table; however, the measured levels from which the averages were calculated are merely provided by a separate glucose tracking time table on a different screen. Accordingly, it is not always clear to a patient as to which values are the constituent values of a particular average. This is disadvantageous when a patient is determining whether an adjustment is needed in his insulin dosage. This problem is illustrated by the following hypothetical situations.

By way of an example, if a lunchtime average was calculated at 180 mg/dl, and the constituent values of the lunchtime average were 162 mg/dl, 204 mg/dl and 174 mg/dl, a patient could safely increase the breakfast dose of a short acting insulin by a small amount since the constituent values had little variation. If, however, the constituent values varied significantly (e.g., were 75 mg/dl, 297 mg/dl and 168 mg/dl), the patient could not safely increase the breakfast dose of a short acting insulin, not even by a small amount. A patient would need to instead decide why there was so much variation, whether it be changes in diet, exercise or stress level. Thus, a need exists for a glucose monitoring device that provides a patient with convenient and immediate access to glucose level averages over relatively short periods of time and to the constituent values that generated the averages in order to make meaningful and timely decisions regarding his insulin regimen and other diabetes management techniques.

SUMMARY OF THE INVENTION

In accordance with an aspect of the present invention, a method for annunciating a patient's medical data levels using a medical data level monitoring device comprises the steps of: (1) storing medical data levels with the corresponding dates and times of day the respective medical data levels were taken; (2) calculating an average medical data level from at least a first medical data level and a second medical data level selected from the stored medical data levels; (3) annunciating the average medical data level; (4) receiving a first user input to annunciate the first medical data level; (5) annunciating the first medical data level; (6) receiving a second user input to annunciate the second medical data level; and (7) annunciating the second medical data level. The annunciating steps for annunciating the average medical data level, the first medical data level and the second medical data level, respectively, can be performed by displaying them on a display device, or by generating an audible sound via a speaker. The medical data levels are preferably blood glucose levels, and the medical data level monitoring device is preferably a blood glucose meter. More than two medical data levels can be used, that is, n medical data levels wherein n is greater than 2.

In accordance with another aspect of the present invention, a variability indicator is provided that indicates the variability between the n medical data levels used to generate the average medical data level. The variability indicator is at least one of a scalar value, and a statistical parameter selected from the group consisting of a standard deviation and a coefficient of variance.

In accordance with yet another aspect of the present invention, the average medical data level and the constituent values are displayed on a display screen. The display screen comprises a first area for displaying one of the average medical data level and the constituent values, and a second area configured to have n indicators corresponding to respective ones of the n medical data levels. Each of the n indicators is displayed as a nonflashing item when the first area is displaying the average medical data level. The corresponding one of the n indicators is flashed when its corresponding n medical data level is being displayed as one of the constituent values. The display screen comprises a third area for displaying a time of day and a date for a corresponding one of the n medical data levels when it is being displayed as a constituent value in the first area.

In accordance with still yet another aspect of the present invention, calculating the average comprises selecting the stored medical data levels used to determine the average medical data level based on the date and time of day the stored medical data levels were taken. A user can define a time period during a day when the average medical data level is desired for that time period on each of a selected number of days (e.g., preferably three days). Calculating the average further comprises the steps of: (1) receiving a user input requesting an average medical data level of the time period for a selected number of days beginning with the current day; (2) determining if the time period has been entered or passed on the current day; (3) using a reading of an medical data level taken during the time period for the current day when determining the average medical data level if the time period has been entered or has passed for the current day; and (4) selecting a stored medical data level taken on the previous day when determining the average medical data level if the time period has yet not been entered or passed for the current day. The using step (3) further comprises the step of selecting one of the earliest and the most recent of a plurality of readings taken on the current day during the time period based on their respective times of day. The selecting step (4) further comprises the step of selecting one of the earliest and the most recent of a plurality of readings taken on the previous day during the time period based on their respective times of day. The using step (3) further comprises the step of using a stored medical data level from the previous day if no valid medical data levels are available from the time period for the current day. The selecting step (4) further comprises the step of using a stored medical data level from the day before the previous day if no valid medical data levels are available from the time period for the previous day.

In accordance with an embodiment of the present invention, an apparatus for patient condition monitoring comprises: (1) a reader for measuring a selected medical data level for the patient; (2) a memory device for storing a plurality of the medical data levels along with their respective dates and time of day they were taken; (3) an annunciator; (4) a user input device; and (5) a processing device connected to the reader, the memory device, the annunciator and the user input device and programmable to calculate an average medical data level from at least a first medical data level and a second medical data level selected from the stored medical data levels in the memory device, to annunciate the average medical data level via the annunciator, to receive a first user input from the user input device to annunciate the first medical data level, to annunciate the first medical data level in response to the first user input, to receive a second user input from the user input device to annunciate the second medical data level, and to annunciate the second medical data level in response to the second user input.

In accordance with another aspect of the present invention, a method of displaying blood glucose levels using a blood glucose meter comprises the steps of: (1) storing blood glucose levels with the corresponding dates and times of day the respective blood glucose levels were taken; (2) calculating an average blood glucose level from at least three of the stored blood glucose levels as the constituent values; (3) displaying the average blood glucose level using a display device of the blood glucose meter; (4) receiving a first user input to display a first one of the constituent values; (5) displaying the first one of the constituent values in response to the first user input; (6) receiving a second user input to display a second one of the constituent values; and (7) displaying the second one of the constituent values in response to the second user input.

In accordance with another aspect of the present invention, a method of displaying blood glucose levels using a blood glucose meter comprises the steps of: (1) storing blood glucose levels with the corresponding dates and times of day the respective blood glucose levels were taken; (2) calculating an average blood glucose level from at least a three of the stored blood glucose levels as the constituent values; (3) displaying the average blood glucose level using a display device of the blood glucose meter; and (4) displaying the constituent values at least one of substantially simultaneously with the average blood glucose level, and after the average blood glucose level using sequential display screens for respective ones of the average blood glucose level and the constituent values that can be generated in a round robin manner.

BRIEF DESCRIPTION OF THE DRAWINGS

These and other objects, advantages and novel features of the present invention will be readily appreciated from the following detailed description when read in conjunction with the accompanying drawings, in which.

Throughout the drawing figures, like reference numerals will be understood to refer to like parts and components.

DETAILED DESCRIPTION OF THE PREFERRED EMBODIMENTS

In accordance with the present invention, a blood glucose meter 100 is provided with advantageous operations, including the determination and display of an effective mealtime average (EMA) or similar average over another user-defined period, the convenient and immediate display of the constituent values used to determine the average, and optional determination and display of variability among the constituent values (e.g., a standard deviation value). The blood glucose meter 100 is exemplified by the Logic™ blood glucose monitor and the Latitude™ diabetes management system available from Becton Dickinson and Company.

Figure 1:
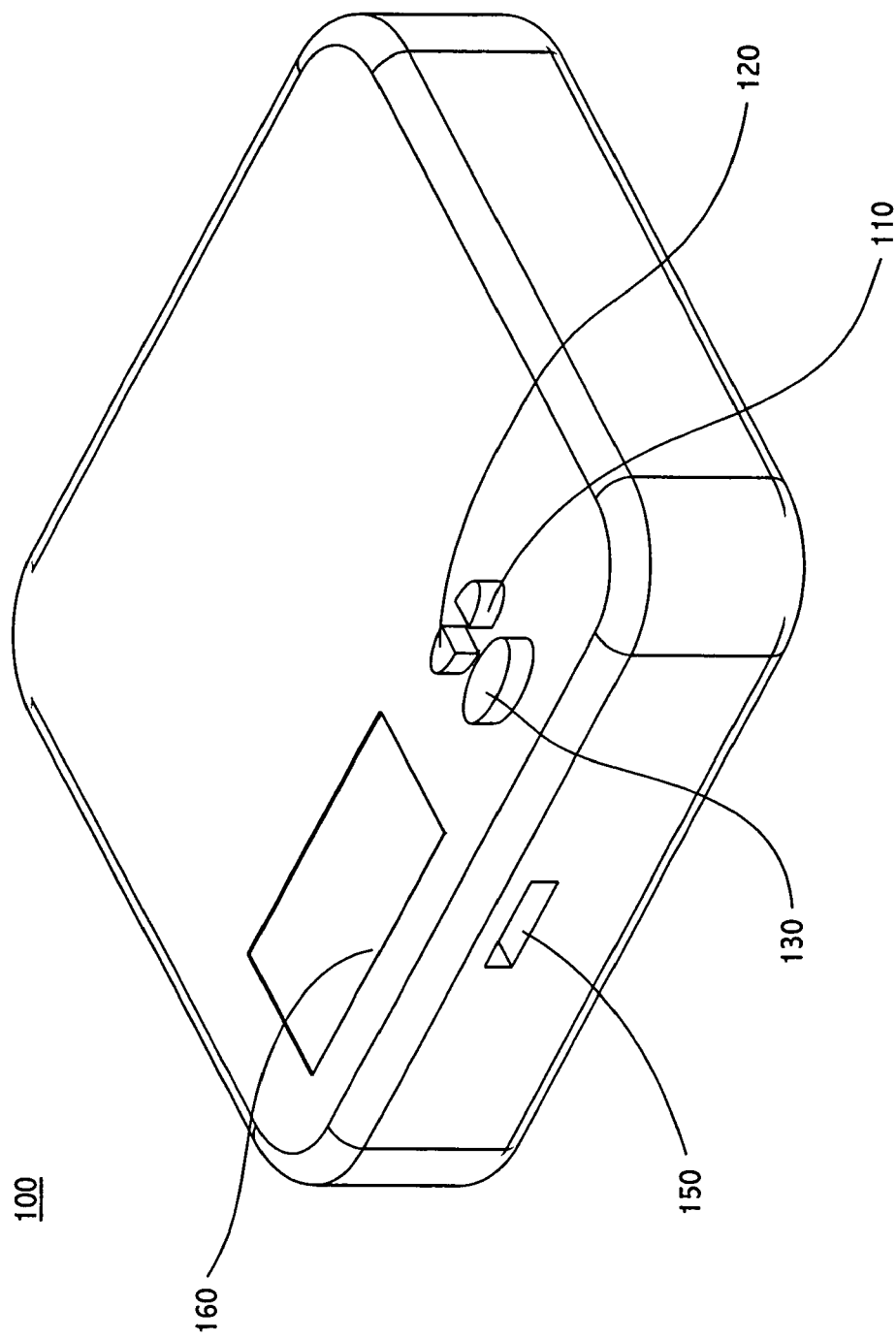
FIG. 1 is a perspective view of an exemplary blood glucose meter in accordance with an embodiment of the present invention.

With reference to FIG. 1, the blood glucose meter 100 of the present invention has a blood glucose sensing area 150 for the monitoring of glucose within a patient. Blood glucose sensing area 150 may utilize a variety of well known means for the monitoring of glucose within a patient. One method may be the use of a disposable strip with reagents applied thereto for the sensing of glucose within a bodily fluid. In an alternate embodiment of the present invention, sensing area 150 could utilize well known non-invasive sensing methods for the determination of glucose within a patient's body. Sensing of glucose by sensing area 150 can be intermittent or continuous. Blood glucose meter 100 also can be configured to be wearable by the patient.

Figure 2:
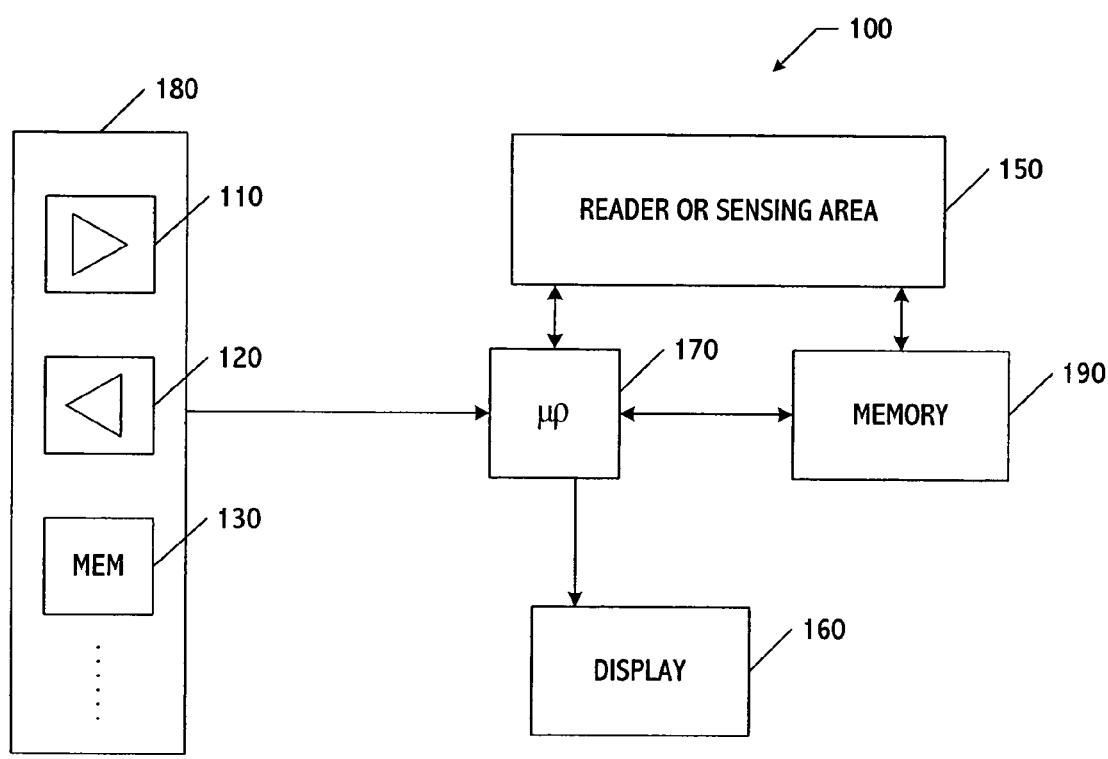
FIG. 2 is a block diagram of the blood glucose meter in FIG. 1.

With reference to FIGS. 1 and 2, blood glucose meter 100 also has a liquid crystal display (LCD) or other type of display device 160 which communicates data within the blood glucose meter 100 to the patient through a variety of menus programmed within the software/program instructions contained within the microprocessor 170 (FIG. 2) of blood glucose meter 100 or stored in the memory device 190 for execution by the microprocessor 170. Alternatively, the meter 100 can annunciate blood glucose values and other information audibly via a speech processing device and speaker. The memory device 190 can store the blood glucose values measured by the reader or other sensing device 150, along with the dates and times of day they were measured, the stored blood glucose values that are selected to be constituent values of an average, and calculated values such as the averages and indicators of variability, among other information. It is to be understood that other memory configurations can be used without departing from the scope of the present invention.

Blood glucose meter 100 also has a variety of input buttons 110, 120, 130 which allow the patient to move through various screens displayed on LCD 160 to view various data within blood glucose meter 100. Forward button 110 and backward button 120 allow patients to move forward and backward through the menu screens shown on LCD 160. Also shown on blood glucose meter 100 is a memory button 130 which allows the user to enter the various menus generated by the software/program instructions of blood glucose meter 100. At least one input button is required; however, alternate embodiments which contain one or more input buttons with different functions are still within the scope of the present invention. Accordingly, a user input device is indicated generally at 180 in FIG. 2.

The present invention provides an advantageous presentation of glucose data to a person with diabetes from a glucose meter, monitor or continuous glucose sensor 100 in which an effective meal average (EMA) value is presented, followed by two or more of the individual values (i.e., hereinafter referred to as the constituent values) that make up the effective meal average. The effective meal average is comprised of an average value and its constituent values and/or a measure of the variability of the range. The effective meal average encompasses those values that occur at specified times (i.e., herein after referred to as the effective meal average timeframe or EMAT). The EMAT can be, for example, one hour before and one hour after a specified meal time, although the length of time before and after the meal could be different (e.g., 30 minutes or up to three hours), or during a specified interval such as from 10 AM to 2 PM. The average can also be for a post-meal timeframe. The effective meal average is calculated over a limited number of days that occurred previous to the calculation and is preferably calculated over three days, although the calculation can include as many as 13 days. The EMA has a minimum number of values that must be obtained within the time and date ranges, which is preferably three values, although the EMA can be based on as few as two values or as many values as were measured during the date range. The microprocessor 170 also employs an algorithm for excluding any given reading from the average. For example, patients may not want to include values taken after meals (i.e., post-prandial values) or control solution readings done during the specified time range. Patients can use from one to eight effective meal averages on any given date range, but preferably use four EMAs determined, for example, for the breakfast, lunch, supper and bedtime snack time periods. The additional four averages can be used for post-meal averages and an average in the middle of the night. The effective meal average provides improved feedback data for clinical decisions by patients with diabetes who use insulin and need to alter their dose of insulin.

The advantages of the present invention are illustrated by the following examples:

EXAMPLE 1

A Lunchtime EMA is calculated at 180 mg/dl and displayed on the LCD 160. The constituent values of the EMA are 162 mg/dl, 204 mg/dl and 174 mg/dl, which are displayed to the patient on the LCD 160 of the blood glucose meter 100. The EMA and the constituent values are preferably displayed via a series screens, each with a respective one of the values, as will be described below in connection with FIGS. 6 and 7. It is to be understood that displays can be generated with different groupings of the EMA and its constituent values and remain within the scope of the present invention. Since the EMA is 180 and the individual values have little variation, at 162, 204 and 174, a patient could safely increase the breakfast dose of a short acting insulin by a small amount, for example, 1 unit.

EXAMPLE 2

A Lunchtime EMA is calculated at 180 mg/dl. The constituent values of the EMA are 75 mg/dl, 297 mg/dl and 168 mg/dl which are displayed to the patient on the LCD 160 of the blood glucose meter 100 preferably via a series of screens. Since the EMA is 180 and the individual values have significant variation, at 75, 297 and 168, a patient could not safely increase the breakfast dose of a short acting insulin, even by a small amount such as 1 unit. A patient could then decide why there is so much variation, whether it be changes in diet, exercise or stress level.

EXAMPLE 3

A Lunchtime EMA is calculated at 180 mg/dl. The constituent values of the EMA are 162 mg/dl, 204 mg/dl and 174 mg/dl which are displayed to the patient on the LCD 160 of the blood glucose meter 100, along with an EMA indicator (e.g., a standard deviation). Since the EMA is 180 and the individual values have little variation, at 162, 204 and 174, as indicated by the EMA indicator, a patient could safely increase the breakfast dose of a short acting insulin by a small amount, for example, 1 unit.

EXAMPLE 4

A Lunchtime EMA is calculated at 180 mg/dl. The constituent values of the EMA are 75 mg/dl, 297 mg/dl and 168 mg/dl which are displayed to the patient on the LCD 160 of the blood glucose meter 100, along with an EMA indicator (e.g., a standard deviation). Since the EMA is 180 and the individual values have great variation, at 75, 297 and 168, as indicated by the EMA indicator, a patient could not safely increase the breakfast dose of a short acting insulin, even by a small amount such as 1 unit. A patient could then decide why there is so much variation, whether it be changes in diet, exercise or stress level.

As indicated by the foregoing examples, in accordance with one aspect of the present invention, the EMA is an array which consists of the average of a series of specific (i.e., with respect to time and other criteria) blood glucose measurements, along with the values which constitute the average. In accordance with another embodiment of the present invention, the EMA is an average of a series of specific (i.e., with respect to time and other criteria) blood glucose measurements, along with an indicator of the variability of the specific measurements.

Prior art devices such as the Glucometer DEX2 mentioned in the background section above create averages for specific user settable times, but do not give the patient any indication of the inherent variability of the readings within the specific times. The patent is then unable to make clinical decisions based on the data. The patient only has an average of the readings of the last 14 days and may make a mistake in judgement with respect to the amount of change of insulin dosage. By contrast, the present invention advantageously communicates the variability dimension of the data. The present invention provides an apparatus and a method to present the data in such a format such that the patient has an average of the glucose readings, the constituent values used to generate the average, and optionally an indication of the variability in readings over the period in question (e.g., the effective meal average timeframe). Also, in accordance with another advantageous aspect of the present invention, the period of data for review is much shorter than existing blood glucose monitoring devices, allowing for a clinical judgement which is based on more recent and relevant data, rather than a running average provided by the existing devices.

Figure 3:
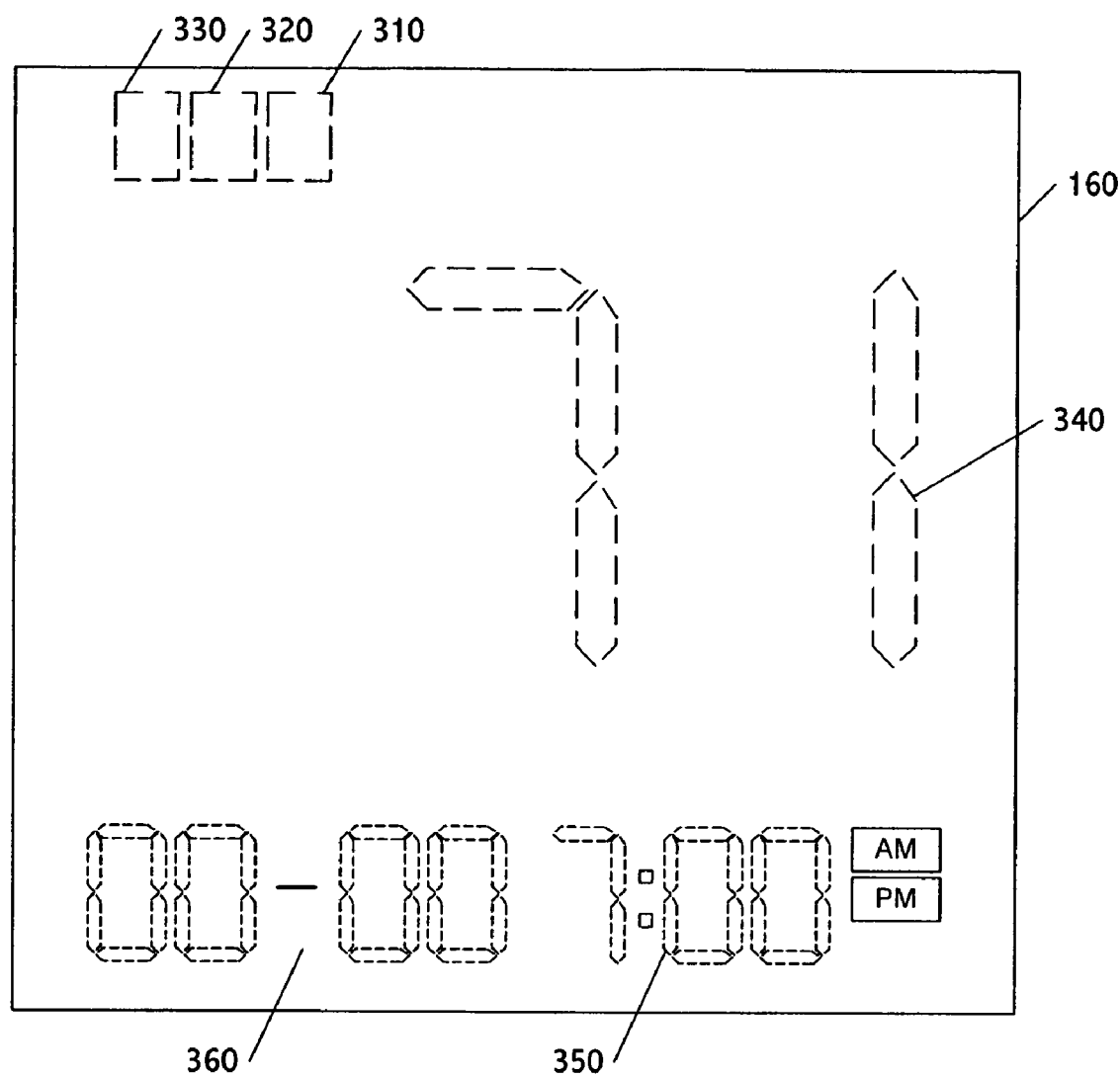
FIG. 3 depicts a display configuration for a blood glucose meter in accordance with an embodiment of the present invention.

Reference is now made to FIG. 3, which depicts an illustrative display configuration for LCD or other display device 160 to display an EMA, or a constituent value or other blood glucose measurement data point, as indicated at 340. Also shown on LCD 160 are first indicator block 310, second indicator block 320, and third indicator block 330. Time value 350 displays the time of the glucose measurement represented by data value 340. A date value can optionally be provided, as indicated at 360. As stated above, it is to be understood that displays can be generated with different groupings of the EMA and its constituent values and remain within the scope of the present invention.

Figure 5:
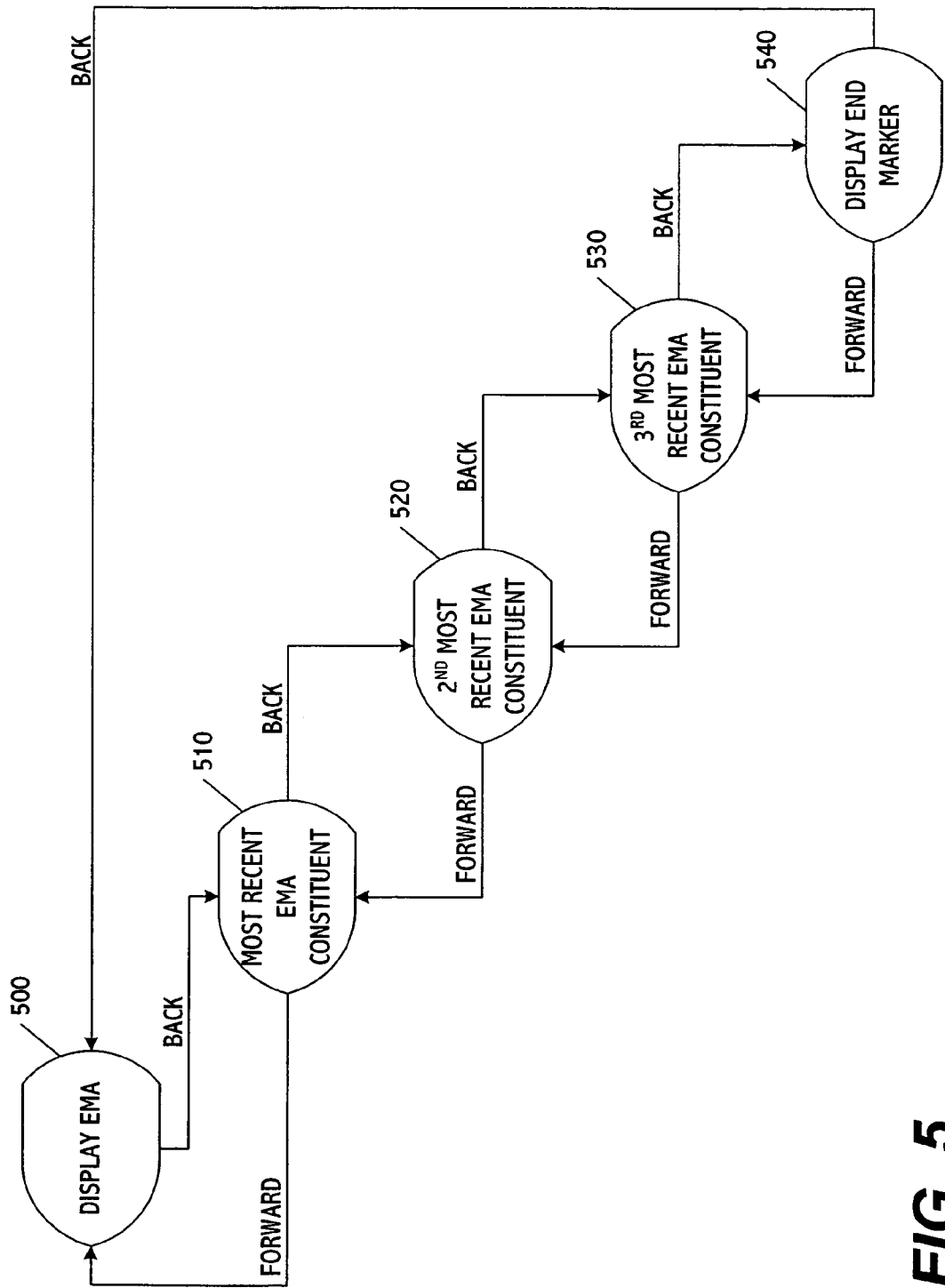
FIG. 5 is a flow chart depicting a sequence of operations for generating displays to communicate an effective meal average and its constituent values in accordance with an embodiment of the present invention.

With reference to FIGS. 3 and 5, in order to indicate the EMA, indicator blocks 310, 320, 330 are all displayed and non-flashing. When the first constituent value of the EMA is displayed as data value 340, as denoted by box 510 in FIG. 5, the first constituent value's measured time is displayed as time value 350, and first indicator block 310 is flashing. When the second constituent value of the EMA is displayed as data value 340, as denoted by box 520 in FIG. 5, the second constituent value's measured time is displayed as time value 350, and second indicator block 320 is flashing. When the third constituent value of the EMA is displayed as data value 340, as denoted by box 530 in FIG. 5, the third constituent value's measured time is displayed as time value 350, and third indicator block 330 is flashing.

Figure 4:
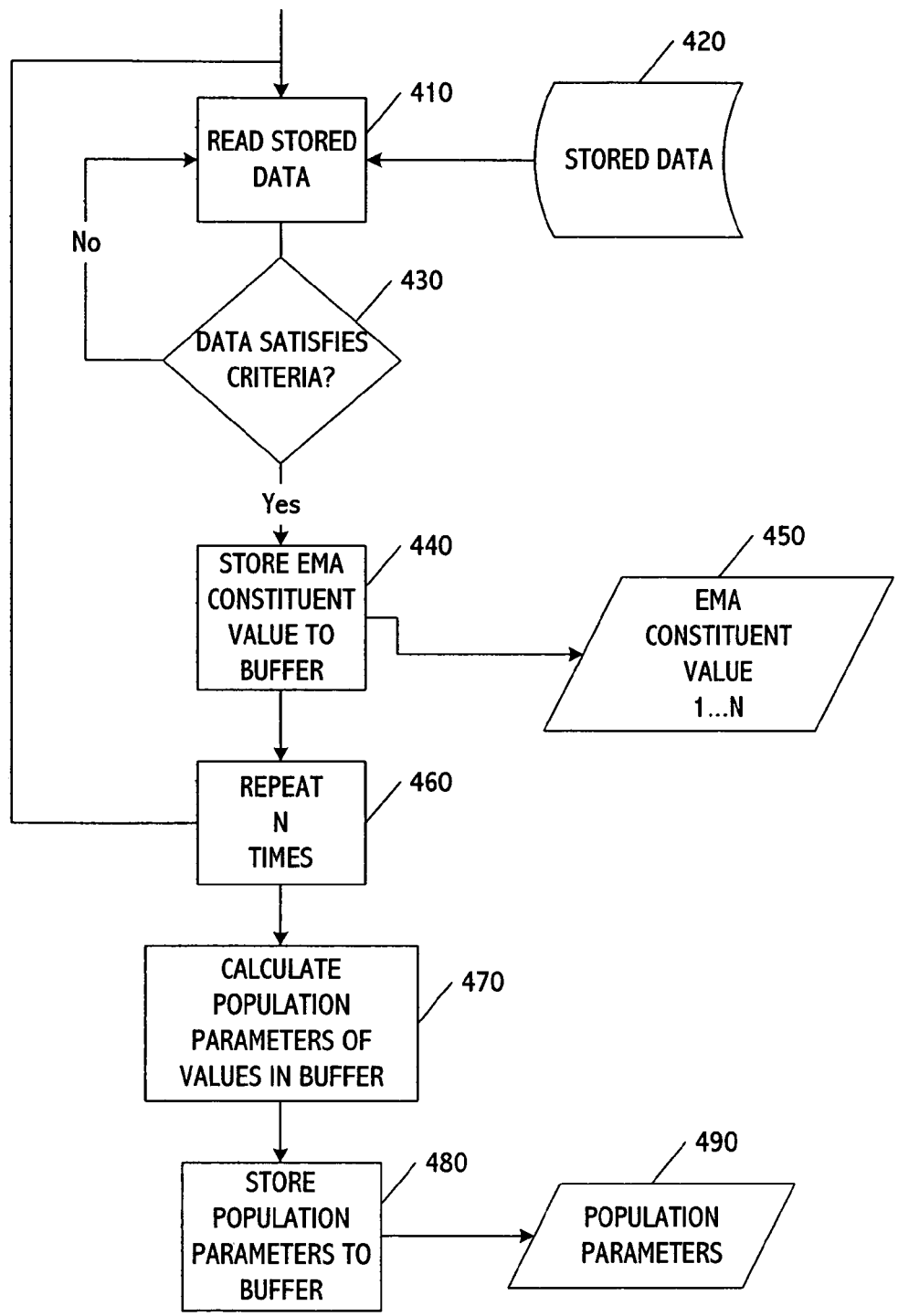
FIG. 4 is a flow chart depicting a sequence of operations for selection of effective meal average constituent values in accordance with an embodiment of the present invention.

FIG. 4 is a flowchart depicting a sequence of operations for the selection of EMA constituent values by the microprocessor 170. The software/program instructions for the meter 100 enters an EMA calculation mode. A single data point is read (step 410) from stored data (step 420) such as data stored in the memory device 190. The stored data is preferably an array of values representing blood glucose measurements, and associated time code information for each measurement, and various other flags. Each data point is compared to criteria (step 430) for checking the data point for its suitability for use in a specific EMA calculation. These criteria can include values and flags corresponding to specific time frames corresponding to the desired EMAT, date information, calibration check information, post-prandial measurement, and specifically user-flagged values, among other criteria. Preferably, in order for the data point to be used as a constituent value for the EMA, the data point is within the EMAT, a pre-prandial measurement, not a calibration check, and not specifically flagged by the user. Once a data point is found that meets the criteria in step 430, the software/program instructions provide for storing the data point (step 440) to a corresponding buffer indicated at 450. The process is repeated (step 460) n times until n EMA constituent values are stored to the constituent value buffer 450, where n can be from 2 to 14, for example, and more preferably n is 3. When n values have been selected, the microprocessor 170 executing the software/program instructions calculates population parameters (step 470) of the constituent values within the constituent values buffer 450, and stores the population parameters (step 480) to a population parameters buffer indicated at 490. At a minimum, the population parameters buffer 490 contains the average of the constituent values 450. Population parameters buffer 490 can additionally contain a standard deviation of the constituent values 450 or another statistical parameter (e.g., scalar value, coefficient of variance, and the like) which represents the variation of the constituent values 450.

As shown in FIG. 5, a series of menu screens are preferably displayed by LCD 160 of the blood glucose meter 100. The effective mealtime average is communicated to the patient via LCD 160. The patient navigates the menus displayed on the LCD 160 by depressing the input buttons 110,120,130. The effective meal average screen in FIG. 5 is represented by box 500. Once at the effective meal average screen 500, which displays an average of the readings for the effective meal average timeframe, the user can then look at the data values which comprise the effective meal average by depressing backward button 120 to reach effective the meal average first constituent value screen denoted by box 510. If the user depresses the forward button 110, the LCD 160 displays the effective meal average screen 500 again. While on effective meal average first value screen 510, if the user depresses backward button 120, the LCD 160 displays a effective meal average second constituent value screen 520. With another press of backward button 120, the LCD 160 displays an effective meal average third constituent value screen 530. With another press of backward button 120, an end marker screen 540 is displayed, which indicates to the patient that the last value seen was the last value of the EMA. While on end marker screen 540, if the user depresses backward button 120, LCD 160 reverts to the effective meal average screen 500 at which point the patient has seen all constituent values from which the effective meal average was derived. Alternatively, this process can be repeated as needed to display any number of constituent values. The constituent values can also be displayed substantially simultaneously with the average blood glucose level (e.g., on the same screen), or substantially immediately before and after the average blood glucose level using sequential display screens for respective ones of the average blood glucose level and the constituent values that can be generated in a round robin manner.

In accordance with an embodiment of the present invention, effective meal average calculation and display are enabled when a Setup.Average function is set to 'ON' within the software/program instructions of the meter 100. Four effective meal averages corresponding to four effective meal average timeframes are preferably viewed in sequence. Preferably, the time span covered in an effective meal average is defined as the center time of that average, plus or minus one hour. For example, a mealtime average whose 'center time' is 7:15 AM covers blood glucose readings from 6:15 AM to 8:15 AM. In an alternate embodiment of the invention, the center time of the effective meal average timeframes is settable by the user.

Figure 6:
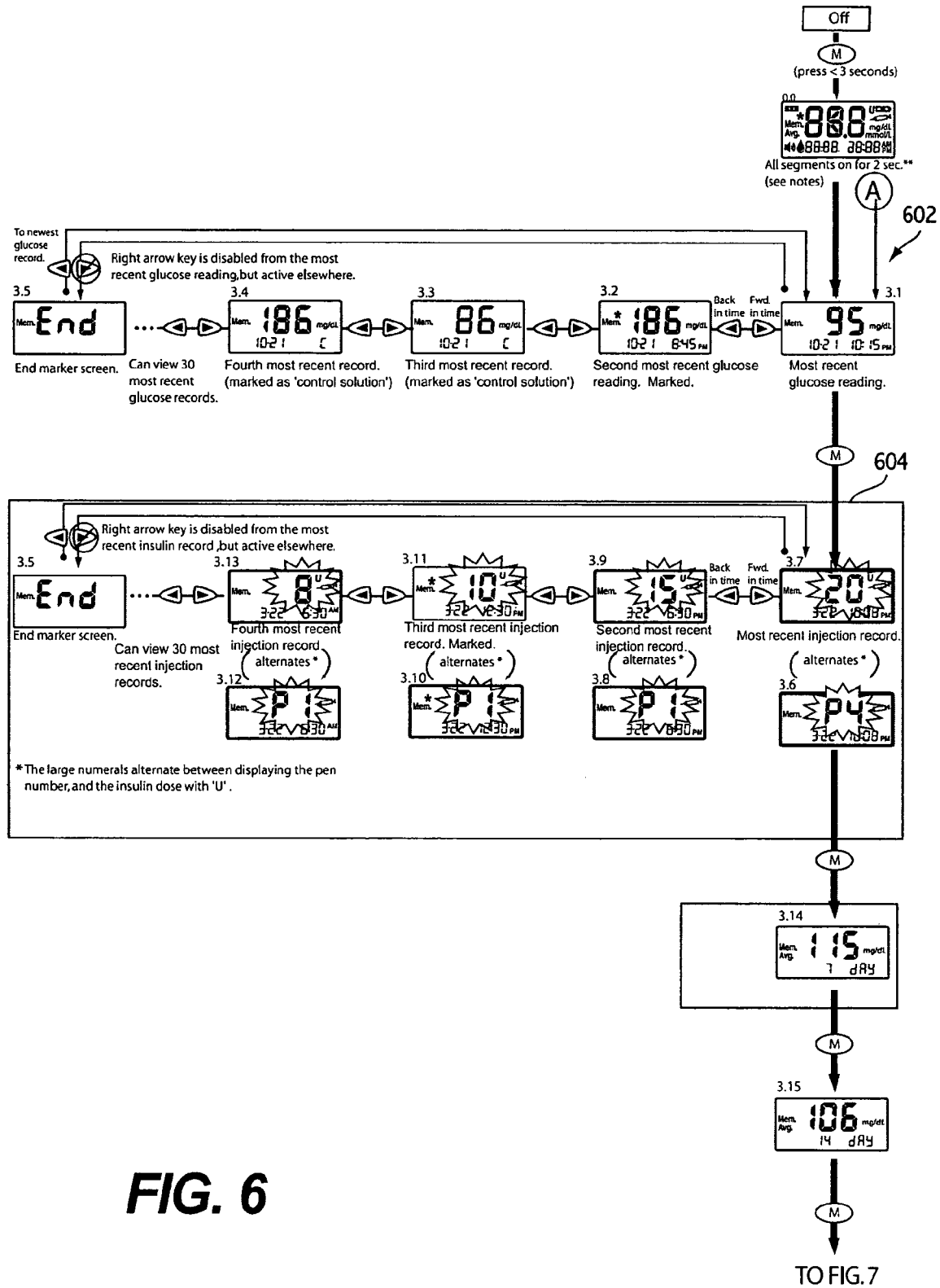
FIGS. 6 and 7 illustrate a series of exemplary screens generated by a blood glucose meter in accordance with an embodiment of the present invention.

In accordance with an embodiment of the present invention, each average is calculated preferably using three readings. One reading is selected per day and begins with the current day if the current time has already entered or passed the time span for that time block. If the current time has not yet entered the time span covered in the specified time block (e.g., the EMAT), then the software/program instructions begin with that same time span on the previous day. If there is more than one reading within the time span on a given day, the software/program instructions select the most recent unmarked reading. In an alternative embodiment, the earliest reading is selected. Marked readings are excluded from averages such as control solution readings, which are marked with a "C" at 350 (FIG. 3) of the LCD 160, as shown in FIG. 6. Other marked readings to be excluded (e.g., by choice of the patient) are marked with an "*". If, on a given day, no readings are found within the time span, the software/program instructions for the meter 100 searches the readings from the previous day. The software/program instructions go back a maximum of five days from the first and most recent time span searched. If fewer than three valid readings are found, the software/program instructions control the display device 160 to appear as " - - - " for that meal time average, indicating that there were not enough readings available to calculate an average from that time block. If there are three valid readings, the meal time average is calculated.

In an alternate embodiment of the invention, the meter 100 can display a standard deviation or other statistical parameter of the EMA data to the patient to indicate the variability of the average for the effective meal average timeframe in question. This indicator of variability is preferably referred to as an EMA indicator. Such statistical parameters can be either a standard parameter (e.g., a standard deviation, coefficient of variance, and the like), or a scalar value (e.g., a scaled value from 1 to 10 etc.), which represents the variability inherent in the data.

Figure 7:
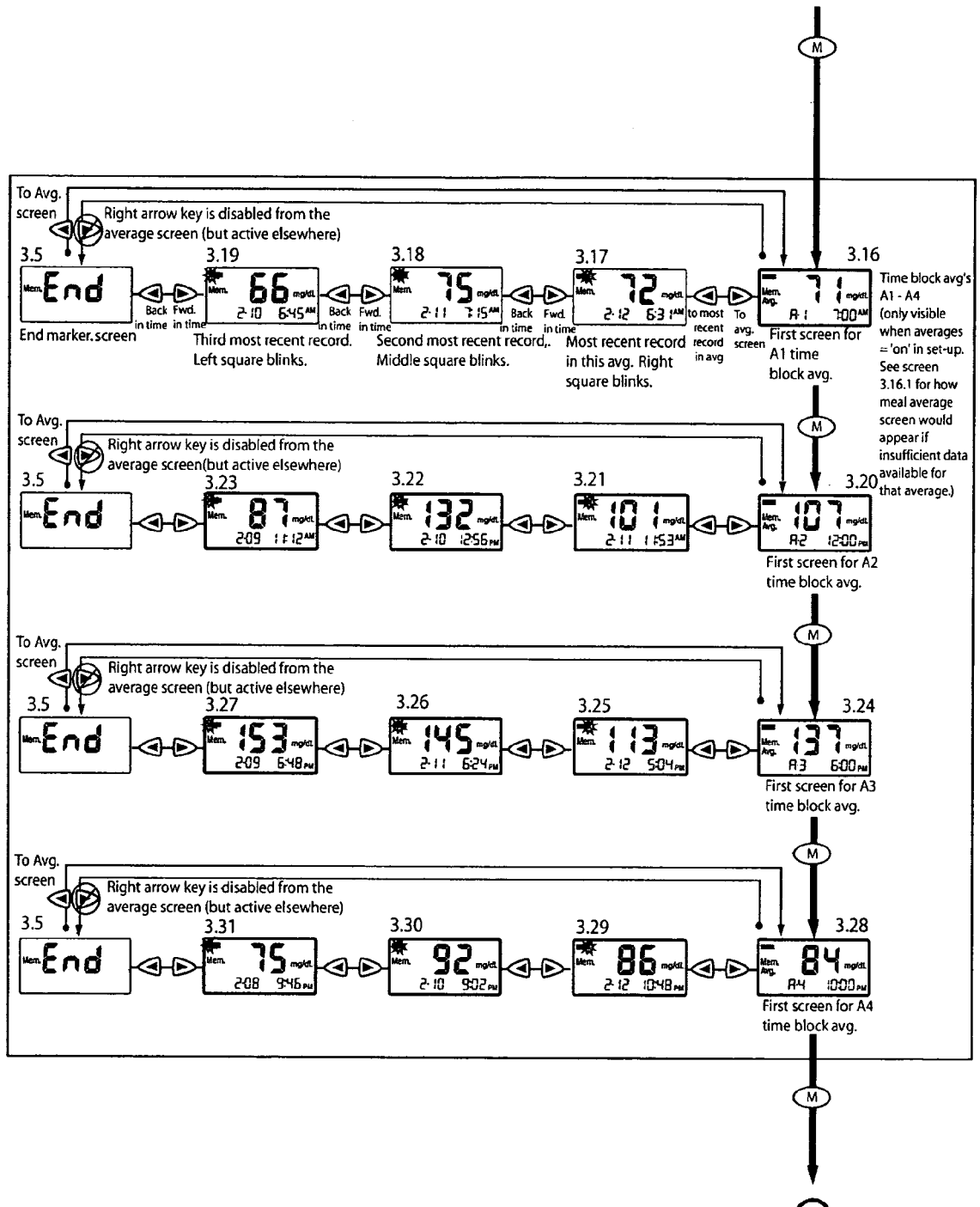

Reference is now made to the exemplary series of display screens on a display device 160 depicted in FIGS. 6 and 7. Screen 0.0 depicts the different possible screen areas that are selectively populated with information, as illustrated throughout FIGS. 6 and 7, depending on the mode selected by the user. The series of display screens indicated generally at 602 in FIG. 6 are for viewing individual blood glucose readings and are accessed by depressing the memory button 130. For example, screen 3.1 is the most recent glucose reading. The forward and backward keys 110 and 120, respectively, can be used to navigate among the most recent readings (e.g., 30 readings) in the memory device 190. These screens comprise "MEM" to indicate that a stored value is being viewed, the glucose level in units mg/dl, and the date and time of the reading. Screens 3.2 and 3.3 illustrate marked readings that are not used for averaging, as indicated by the "*" and the "C" in their respective screens.

The series of display screens indicated generally at 604 in FIG. 6 are for viewing insulin injections and are preferably only visible when insulin is set to be "ON" set-up of the meter 100. They can be accessed, for example, by depressing the memory button 130 when the current glucose reading is displayed. The large numerals are indicated along with a syringe icon, and alternate between displaying the pen number and the insulin dose, which is also indicated along with a "U". The date and time of day of the injection are also indicated.

The memory button 130 can be depressed again to obtain a 7-day average reading, and depressed again to obtain a 14-day average reading. Screen 3.14 provides a 7-day average, and includes the reading in units mg/dl and the indication of "7 day". Screen 3.15 provides a 14-day average, and includes the reading in units mg/dl and the indication of "14 day".

With reference to FIG. 7, the memory button 130 can be depressed again to obtain a time block average (e.g., an EMA). A first screen 3.16 provides a breakfast EMA. The forward and backward keys 110 and 120 allow the user to view the constituent values on the screens 3.17 through 3.19, which represent valid data taken over the most recent three days (e.g., February 10, 11 and 12) and during the breakfast EMAT for each day. Another depression of the memory button 130 provides a lunchtime EMA screen 3.20. The forward and backward keys 110 and 120 allow the user to view the constituent values on the screens 3.21 through 3.23, which represent valid data taken over the most recent three days (e.g., February 9, 10 and 11) and during the lunchtime EMAT for each day. Another depression of the memory button 130 provides a dinnertime EMA screen 3.24. The forward and backward keys 110 and 120 allow the user to view the constituent values on the screens 3.25 through 3.27, which represent valid data taken over the most recent three days (e.g., February 9, 11 and 12) and during the dinnertime EMAT for each day. As stated above, if no valid data is available for the dinnertime EMAT on a given day (e.g., February 10), then the microprocessor 170 is programmed to use data from the previous day, February 9. Finally, another depression of the memory button 130 provides a nighttime EMA screen 3.28. The forward and backward keys 110 and 120 allow the user to view the constituent values on the screens 3.29 through 3.31, which represent valid data taken over the most recent three days (e.g., February 8, 10 and 12) and during the nighttime EMAT for each day.

It is to be understood that the toggling between viewing modes (e.g., individual blood glucose readings, insulin injection readings, 7-day average reading, 14-day average reading, and time block averages (e.g., EMAs) by depressing the memory button can be ordered differently than shown in FIGS. 6 and 7, or include more or fewer information viewing modes. Further, the meter 100 can be provided with different user buttons or other input devices that allow direct access to any of the information viewing modes (e.g., selection from a menu of information display options provided on the LCD 160).

The following represents exemplary code for implementing an embodiment of the present invention.

1.1.1 Meal Time Average Button Functions

1.1.1.1 Static DisplayMealBars(void)

This function displays meal bar annunciators.

```
Turn ON meal bar 1, 2 and 3 annunciators
If record counter = 1
    Enable flashing for meal bar 1 annunciator
    Disable flashing for meal bar 2 annunciator
    Disable flashing for meal bar 3 annunciator
Else if record counter = 2
    Disable flashing for meal bar 1 annunciator
    Enable flashing for meal bar 2 annunciator
    Disable flashing for meal bar 3 annunciator
Else if record counter = 3
    Disable flashing for meal bar 1 annunciator
    Disable flashing for meal bar 2 annunciator
    Enable flashing for meal bar 3 annunciator
```

1.1.1.2 Static Void M_UiMealTimeAverage(TBNum)

This function displays the Time Block's center time and average. If the average cannot be calculated, the meter displays ' - - - '.

```
Input: TBNum, time block number
Display Setup.CTime[TBNum].Hours
Display Setup.CTime[TBNum].Minutes
Call IntervalAverage routine, to calculate time block average
If IntervalAverage result < 0 Display '---'
Else
    Display IntervalAverage result
    Clear record counter
    Call DisplayMealBars, to display meal bar annunciators
```

1.1.1.3 Static Void L_UiMealThneAverage(TBNum)

This function displays an older glucose record used for averaging or the time block average. If the average cannot be calculated, the meter displays ' - - - '.

| Action | Current Display | Next Display |
|---|---|---|
| Left arrow Button press | '---' (Can't calculate average) | No change |
| | Time Block Average | Glucose Record No. 1 |
| | Glucose Record No. 1 | Glucose Record No. 2 |
| | Glucose Record No. 2 | Glucose Record No. 3 |
| | Glucose Record No. 3 | 'End' |
| | 'End' | Time Block Average |

```
Input: TBNum, time block number
If IntervalAverage result > 0
    Increment record counter
    Clear display
    If record counter > 4
        Clear record counter
        Display Setup.CTime[TBNum].Hours
        Display Setup.CTime[TBNum].Minutes
        Display IntervalAverage result
        Call DisplayMealBars, to display meal bar annunciators
    Else if record counter = 4
        Display 'End'
    Else
        Display glucose record indexed by the record counter
        Call DisplayMealBars, to display meal bar annunciators
```

1.1.1.4 Static Void R_UiMealThneAverage(1'BNum)

This function displays a newer glucose record used for averaging or the time block average. If the average cannot be calculated, the meter displays ' - - - '.

| Action | Current Display | Next Display |
|---|---|---|
| Right arrow Button press | '---' (Can't calculate average) | No change |
| | Time Block Average | No change |
| | Glucose Record No. 1 | Time Block Average |
| | Glucose Record No. 2 | Glucose Record No. 1 |
| | Glucose Record No. 3 | Glucose Record No. 2 |
| | 'End' | Glucose Record No. 3 |

```
Input: TBNum, time block number
If IntervalAverage result > 0
    Decrement record counter
    If record counter < 1
        Clear record counter
        Display Setup.CTime[TBN].Hours
        Display Setup.CTime[TBNum].Minutes
        Display IntervalAverage result
    Else
        Display glucose record indexed by the record counter
        Call DisplayMealBars, to display meal bar annunciators
```

1.1.2 A1 Time Block Average

The meter enters this state when Setup.Average is ON, the meter is in the 14-day Average state and the user held the Mode button less than 1.5 seconds.

1.1.2.1 Static Void MUiMealTime1Average(void)

If Set-up.Average is ON, this function displays the time block average. If the average cannot be calculated, the meter displays ' - - - '. If Setup.Average is OFF, this function resets the state machine to the Individual Glucose Reading Review state.

Global Parameters used:
Setup.Average
If Setup.Average is ON
Call M_UiMealTimeAverage(0), to calculate and display block average
Else
UiState=kState1
Call M UiRecallResults, back to Individual Blood Glucose Readings

1.1.2.2 Static Void L_UiMealTime1Average(void)

This function displays an older glucose record used for averaging or the time block average. If the average cannot be calculated, the meter displays ' - - - '.

Call L UiMealTimeAverage(0), to display older averaging glucose record

1.1.2.3 Static Void R_UiMealTime1Average(void)

This function displays a newer glucose record used for averaging or the time block average. If the average cannot be calculated, the meter displays ' - - - '.

Call R_UiMealTimeAverage(0), to display newer averaging glucose record 1.1.3 A2 Time Block Average The meter enters this state when the meter is in the A1 Time Block Average state and the user held the Mode button less than 1.5 seconds.

1.1.3.1 Static Void M_UiMealTime2Average(void)

This function displays the time block average. If the average cannot be calculated, the meter displays ' - - - '.

Call M_UiMealTimeAverage(1), to calculate and display block average 1.1.3.2 Static Void L_UiMealTime2Average(void)

This function displays an older glucose record used for averaging or the time block average. If the average cannot be calculated, the meter displays ' - - - '.

Call L_UiMealTimeAverage(1), to display older averaging glucose record 1.1.3.3 Static Void R_UiMealTime2Average(void)

This function displays a newer glucose record used for averaging or the time block average. If the average cannot be calculated, the meter displays ' - - - '.

Call R_UiMealTimeAverage(1), to display newer averaging glucose record 1.1.4 A3 Time Block Average The meter enters this state when the meter is in the A2 Time Block Average state and the user held the Mode button less than 1.5 seconds.

1.1.4.1 Static Void MUiMealTime3Average(void)

This function displays the time block average. If the average cannot be calculated, the meter displays ' - - - '.

Call M_UiMealTimeAverage(2), to calculate and display block average 1.1.4.2 Static Void L_UiMealTime3Average(void)

This function displays an older glucose record used for averaging or the time block average. If the average cannot be calculated, the meter displays ' - - - '.

Call L_UiMealTimeAverage(2), to display older averaging glucose record 1.1.4.3 Static Void R_UiMealTime3Average(void)

This function displays a newer glucose record used for averaging or the time block average. If the average cannot be calculated, the meter displays ' - - - '.

Call R_UiMealTimeAverage(2), to display newer averaging glucose record 1.1.5 A4 Time Block Average The meter enters this state when the meter is in the A3 Time Block Average state and the user held the Mode button less than 1.5 seconds. In this state, if the Mode button is held less than 1.5 seconds, the state machine resets to the Individual Blood Glucose Results Review state.

1.1.5.1 Static Void M_UiMealTime4Average(void)

This function displays the time block average. If the average cannot be calculated, the meter displays ' - - - '.

Call M_UiMealTimeAverage(3), to calculate and display block average 1.1.5.2 Static Void L_UiMealTime4Average(void)

This function displays an older glucose record used for averaging or the time block average. If the average cannot be calculated, the meter displays ' - - - '.

Call LUiMealTimeAverage(3), to display older averaging glucose record 1.1.5.3 Static Void R_UiMealTime4Average(void)

This function displays a newer glucose record used for averaging or the time block average. if the average cannot be calculated, the meter displays ' - - - '.

Call R UiMealTimeAverage(3), to display newer averaging glucose record

Although the present invention has been described with reference to preferred embodiments thereof, it will be understood that the invention is not limited to the details thereof. Various modifications and substitutions will occur to those of ordinary skill in the art. All such substitutions are intended to be embraced within the scope of the invention as defined in the appended claims.

What is claimed is:

1. A method of annunciating a patient's medical data levels using a medical data level monitoring device comprising the steps of:

storing medical data levels with the corresponding dates and times of day the respective medical data levels were taken;

calculating using a processing device an average medical data level from at least a first medical data level and a second medical data level selected from the stored medical data levels;

annunciating said average medical data level;

receiving a first user input to annunciate said first medical data level;

annunciating said first medical data level;

receiving a second user input to annunciate said second medical data level; and annunciating said second medical data level;

wherein said calculating step further comprises the steps of selecting the stored medical data levels used to determine said average medical data level based on the date and time of day the stored medical data levels were taken;

defining a time period during a day when the average medical data level is desired for that time period on each of a selected number of days;

receiving a user input requesting an average medical data level of said time period for a selected number of days beginning with the current day;

determining if said time period has been entered or passed on said current day;

using a reading of an medical data level taken during the time period for said current day when determining said average medical data level if said time period has been entered or has passed for the current day; and selecting a stored medical data level taken on the previous day when determining said average medical data level if said time period has yet not been entered or passed for the current day.

2. A method as claimed in claim 1, wherein said selected number of days is three.

3. A method as claimed in claim 1, wherein said using step further comprises the step of selecting one of the earliest and the most recent of a plurality of readings taken on said current day during said time period based on their respective times of day.

4. A method as claimed in claim 1, wherein said selecting step further comprises the step of selecting one of the earliest and the most recent of a plurality of readings taken on said previous day during said time period based on their respective times of day.

5. A method as claimed in claim 1, wherein said using step further comprises the step of using a stored medical data level from the previous day if no valid medical data levels are available from said time period for the current day, and said selecting step further comprises the step of using a stored medical data level from the day before said previous day if no valid medical data levels are available from said time period for the previous day.

6. A method as claimed in claim 1, wherein said calculating step further comprises the step of using stored medical data levels from as many as a selected maximum number of previous days if no valid medical data levels are available for said current day.

7. A method as claimed in claim 1, wherein said selected maximum number of days is five.

8. An apparatus for patient condition monitoring comprising:
a reader for measuring a selected medical data level for said patient;
a memory device for storing a plurality of the medical data levels along with their respective dates and time of day they were taken;
an annunciator;
a user input device; and
a processing device connected to said reader, said memory device, said annunciator and said user input device and programmable to calculate an average medical data level from at least a first medical data level and a second medical data level selected from the stored medical data levels in said memory device, to annunciate the average medical data level via said annunciator, to receive a first user input from said user input device to annunciate the first medical data level, to annunciate the first medical data level in response to said first user input, to receive a second user input from said user input device to annunciate the second medical data level, and to annunciate the second medical data level in response to said second user input;
wherein said processing device is programmed to select the stored medical data levels used to determine said average medical data level based on the date and time of day the stored medical data levels were taken;
wherein said processing device is operable to generate prompts via said annunciator to allow a user to define via said user input device a time period during a day when the average medical data level is desired for that time period on each of a selected number of days;
wherein said processing device is further programmed to receive a user input requesting an average medical data level of said time period for a selected number of days beginning with the current day, to determine if said time period has been entered or passed on said current day, to use a reading of an medical data level taken during the time period for said current day when determining the average medical data level if said time period has been entered or has passed for the current day, and to select a stored medical data level taken on the previous day when determining the average medical data level if said time period has yet not been entered or passed for the current day.

9. An apparatus as claimed in claim 8, wherein said selected number of days is three.

10. An apparatus as claimed in claim 8, wherein said processing device is programmable to select one of the earliest and the most recent of a plurality of readings taken on said current day during said time period based on their respective times of day.

11. An apparatus as claimed in claim 8, wherein said processing device is programmable to select one of the earliest and the most recent of a plurality of readings taken on said previous day during said time period based on their respective times of day.

12. An apparatus as claimed in claim 8, wherein said processing device is programmable to use a stored medical data level from the previous day if no valid medical data levels are available from said time period for the current day, and, when selecting a stored medical data level taken on the previous day, to use a stored medical data level from the day before said previous day if no valid medical data levels are available from said time period for the previous day.

13. An apparatus as claimed in claim 8, wherein said processing device is programmable to use stored medical data levels from as many as a selected maximum number of previous ago if no valid medical data levels are available for said current day.

14. An apparatus as claimed in claim 13, wherein said selected maximum number of days is five.

15. A method of displaying blood glucose levels using a blood glucose meter comprising the steps of:
storing blood glucose levels with the corresponding dates and times of day the respective blood glucose levels were taken;
calculating using a processing device an average blood glucose level from at least a three of the stored blood glucose levels as the constituent values;
displaying the average blood glucose level using a display device of said blood glucose meter;
receiving a first user input to display a first one of the constituent values;
displaying the first one of the constituent values in response to the first user input;
receiving a second user input to display a second one of the constituent values; and
displaying the second one of the constituent values in response to the second user input;
wherein said calculating step further comprises the steps of
defining a time period during a day when the average blood glucose level is desired for that time period on each of a selected number of days;
receiving a user input requesting an average blood glucose level of said time period for a selected number of days beginning with the current day;
determining if said time period has been entered or passed on said current day;
using a reading of an blood glucose level taken during the time period for said current day when determining the average blood glucose level if said time period has been entered or has passed for the current day; and
selecting a stored blood glucose level taken on the previous day when determining the average blood glucose level if said time period has yet not been entered or passed for the current day.

16. A method as claimed in claim 15, wherein said selected number of days is three.

17. A method as claimed in claim 15, wherein said using step further comprises the step of selecting one of the earliest and the most recent of a plurality of readings taken on said current day during said time period based on their respective times of day.

18. A method as claimed in claim 15, wherein said selecting step further comprises the step of selecting one of the earliest and the most recent of a plurality of readings taken on said previous day during said time period based on their respective times of day.

19. A method as claimed in claim 15, wherein said using step further comprises the step of using a stored blood glucose level from the previous day if no valid blood glucose levels are available from said time period for the current day, and said selecting step further comprises the step of using a stored blood glucose level from the day before said previous day if no valid blood glucose levels are available from said time period for the previous day.

20. A method as claimed in claim 15, wherein said calculating step further comprises the step of using stored blood glucose levels from as many as a selected maximum number of previous days if no valid blood glucose levels are available for said current day.

21. A method as claimed in claim 20, wherein said selected maximum number of days is five.

22. A method of displaying blood glucose levels using a blood glucose meter comprising the steps of:
   storing blood glucose levels with the corresponding dates and times of day the respective blood glucose levels were taken;
   calculating using a processing devicean average blood glucose level from at least a three of the stored blood glucose levels as the constituent values;
   displaying the average blood glucose level using a display device of said blood glucose meter; and
   displaying the constituent values at least one of substantially simultaneously with said average blood glucose level, and after the average blood glucose level using sequential display screens for respective ones of the average blood glucose level and the constituent values that can be generated in a round robin manner;
   wherein said calculating step comprises the steps of
   selecting the stored blood glucose levels used to determine said average blood glucose level based on the date and time of day the stored blood glucose levels were taken;
   defining a time period during a day when the average blood glucose level is desired for that time period on each of a selected number of days;
   receiving a user input requesting an average blood glucose level of said time period for a selected number of days beginning with the current day;
   determining if said time period has been entered or passed on said current day;
   using a reading of an blood glucose level taken during the time period for said current day when determining the average blood glucose level if said time period has been entered or has passed for the current day; and
   selecting a stored blood glucose level taken on the previous day when determining the average blood glucose level if said time period has yet not been entered or passed for the current day.

23. A method as claimed in claim 22, further comprising the step of displaying a variability indicator that indicates the variability between said constituent blood glucose levels.

24. A method as claimed in claim 23, wherein the variability indicator is at least one of a scalar value, and a statistical parameter selected from the group consisting of a standard deviation and a coefficient of variance.

25. A method as claimed in claim 22, wherein said selected number of days is three.

26. A method as claimed in claim 22, wherein said using step further comprises the step of selecting one of the earliest and the most recent of a plurality of readings taken on said current day during said time period based on their respective times of day.

27. A method as claimed in claim 22, wherein said selecting step further comprises the step of selecting one of the earliest and the most recent of a plurality of readings taken on said previous day during said time period based on their respective times of day.

28. A method as claimed in claim 22, wherein said using step further comprises the step of using a stored blood glucose level from the previous day if no valid blood glucose levels are available from said time period for the current day, and said selecting step further comprises the step of using a stored blood glucose level from the day before said previous day if no valid blood glucose levels are available from said time period for the previous day.

* * * * *

UNITED STATES PATENT AND TRADEMARK OFFICE
CERTIFICATE OF CORRECTION

PATENT NO.        : 7,570,980 B2                                Page 1 of 1
APPLICATION NO.   : 10/658209
DATED             : August 4, 2009
INVENTOR(S)       : Barry H. Ginsberg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1591 days.

Signed and Sealed this

Seventh Day of September, 2010

David J. Kappos
*Director of the United States Patent and Trademark Office*